US00PP18755P2

(12) United States Plant Patent
Bradford

(10) Patent No.: US PP18,755 P2
(45) Date of Patent: Apr. 22, 2008

(54) PEACH TREE NAMED 'WESTERN PRINCESS'

(50) Latin Name: *Prunus persica*
Varietal Denomination: Western Princess

(76) Inventor: Lowell Glen Bradford, 10237 E, Mariposa Way, Le Grand, CA (US) 95333

( * ) Notice: Subject to any disclaimer, the term of this patent is extended or adjusted under 35 U.S.C. 154(b) by 67 days.

(21) Appl. No.: 11/637,867

(22) Filed: Dec. 13, 2006

(51) Int. Cl.
*A01H 5/00* (2006.01)

(52) U.S. Cl. ..... Plt./198

(58) Field of Classification Search ..... Plt./198
See application file for complete search history.

(56) References Cited

U.S. PATENT DOCUMENTS

PP7,066 P 12/1989 Bradford
PP7,421 P 1/1991 Bradford

*Primary Examiner*—Kent Bell

(57) ABSTRACT

The present invention relates to a new and distinct variety of peach tree, *Prunus persica,* broadly characterized by a medium size, vigorous, hardy, self-fertile, productive and regular bearing tree. The fruit matures under the ecological conditions described in early July, with first picking on Jul. 1, 2006. The fruit is uniformly large in size, mildly acidic and sweet in flavor, globose in shape, freestone in type, firm in texture, yellow in flesh color, and mostly red in skin color.

1 Drawing Sheet

Botanical classification: *Prunus persica.*
Variety denomination: 'WESTERN PRINCESS'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of peach tree, which has been denominated varietally as 'WESTERN PRINCESS'. The present variety was hybridized by me in 1992, grown as a seedling on its own root in my greenhouse, and transplanted to a cultivated area of my experimental orchard located near Le Grand, Calif., in Merced County (San Joaquin Valley).

The variety was developed as a first generation cross using 'Diamond Princess' (U.S. Plant Pat. No. 7,066) peach as the selected seed parent and an unnamed white flesh peach (unpatented) as the selected pollen parent. A single tree from the stated cross was selected as the claimed variety. Subsequent to origination of the present variety of peach tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is most similar to its selected seed parent, 'Diamond Princess' (U.S. Plant Pat. No. 7,066) peach, by producing peaches that are nearly globose in shape, freestone in type, yellow in flesh color, acidic and sweet in flavor, and mostly red in skin color, but is distinguished therefrom by requiring much less chilling hours and by producing fruit that is larger in size and that matures about ten days earlier.

SUMMARY OF VARIETY

In summary, the present variety is characterized by a medium size, vigorous, hardy, self-fertile, productive and regular bearing tree. The fruit matures under the ecological conditions described in early July, with first picking on Jul. 1, 2006. The fruit is uniformly large in size, mildly acidic and sweet in flavor, globose in shape, freestone in type, firm in texture, yellow in flesh color, and mostly red in skin color.

DRAWING

The accompanying photograph consists of four whole fruits positioned to display the characteristics of the skin color and form, one fruit divided around the suture plane to reveal the flesh and stone, two insets to reveal buds and blossoms in various stages, and a full size leaf.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm eating ripe on Jul. 10, 2006, on the original tree during its fourteenth growing season. All major color code designations are by reference to the Inter-Society Color Council, National Bureau of Standards. Common color names are also used occasionally.

Tree

Size: Medium, reaching and maintaining a height of 11' [3.35 m.] and a spread of 10' [3.05 m.] after fourteen growing seasons utilizing typical dormant pruning.
Vigor: Vigorous, responding typically to irrigation and fertilization. The variety grows about 3' [0.91 m.] of surplus top-growth during the spring and summer. The plant should be grown on a standard commercial rootstock for production purposes.
Growth: Spreading and dense.
Form: Vase formed.
Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Approximate Chilling Requirement: 500 hours.

Trunk:

*Size.*—Medium, reaching a maximum diameter of 6½" [165 mm.] after the fourteenth growing season.

*Texture.*—Shaggy.

*Bark color.*—A Brownish gray [64. brGy] and Dark reddish brown [44. d.rBr] variegation with Light yellowish brown [76. l.yBr] crevices present.

*Lenticels.*—Approximate Number Per Square Inch: 7. Color: Moderate orange yellow [71. m.OY]. Typical Size: 3/16" [4.8 mm.] to 7/16" [11.1 mm.]. Shape: Eye-shaped to elongated.

Branches:

*Size.*—Diameter of limb is 4" [102 mm.] measured 12" above the crotch, 2¾" [70 mm.] measured 12" above the first fork.

*Texture.*—Smooth on first and second year wood, increasing roughness with age.

*Color.*—1st Year Wood Topside: Grayish red [19. gy.R]. 1st Year Wood Underside: Brilliant yellow green [116. brill.YG]. Older wood: Deep yellowish brown [75. deep yBr].

*Lenticels.*—Number Per Square Inch: More than 50 on second year wood. Color: Light yellowish brown [76. l.yBr]. Typical size: 1/64" [0.4 mm.] to 3/32" [2.4 mm.] on second year wood. Shape: Elongated.

Leaves:

*Size.*—Medium. Average Length: 5¾" [146 mm.]. Average Width: 1¾" [44 mm.].

*Arrangement.*—Alternate.

*Thickness.*—Medium.

*Form.*—Elliptical.

*Apex.*—Acuminate.

*Base.*—Acute, with a base angle of 75 to 80 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: ¼" [6.4 mm.]. Average Thickness: 1/16" [1.6 mm.]. Color: Very yellow green [115. v.YG].

*Stipules.*—Number: Usually 2 per leaf, up to 6 per growing tip. Average Length: 5/16" [7.9 mm.]. Color: Very yellow green [115. v.YG] becoming Moderate reddish brown [43. m.rBr] with maturity.

*Glands.*—Number: 2 to 4 per leaf. Position: Alternately positioned on petiole and base of blade. Size: Medium. Form: Reniform. Color: Brilliant yellow green [116. brill.YG] becoming Dark yellowish brown [78. d.yBr] with age.

*Leaf buds.*—Pointed, medium in size.

Flower buds:

*Hardiness.*—Hardy, with respect to central California winters.

*Diameter.*—Typically ⅜" [9.5 mm.] 1 week before bloom.

*Length.*—Typically 9/16" [14.3 mm.] 1 week before bloom.

*Form.*—Not appressed.

*Surface.*—Pubescent.

*Color.*—Moderate purplish pink [250. m.pPk].

Flowers: Perfect, complete, perigynous, usually a single pistil, typically thirty or more stamens, five sepal and petal locations alternately positioned.

*Type.*—Showy, very large.

*Average flower diameter.*—2" [50.8 mm.].

*Number of petals.*—Usually five, but extra petal fragments and full double blossoms occur occasionally.

*Petal shape.*—Circular to oval.

*Petal margin.*—Somewhat wavy.

*Average petal diameter.*—13/16" [20.6 mm.].

*Average petal length.*—⅞" [22.2 mm.].

*Petal apex.*—Rounded.

*Petal base.*—Rounded to somewhat truncate.

*Petal color.*—Pale pink [7. p.Pk] toward the apex, Light purplish pink [249. l.pPk] toward the base.

*Anther color.*—Dark red [16. d.R] over a Light yellow [86. l.Y] center at bloom onset.

*Stigma color.*—Light greenish yellow [101. l.gY].

*Sepal color.*—Dark purplish red [259. d.pR].

*Sepal length.*—¼" [6.4 mm.].

*Sepal width.*—3/16" [4.8 mm.].

*Average pistil length.*—⅞" [22.2 mm.].

*Average stamen length.*—⅝" [15.9 mm.].

*Fragrance.*—Moderate.

*Blooming period.*—Early, five days before 'Rose Diamond' (U.S. Plant Pat. No. 7,421) nectarine.

*Onset of bloom.*—One percent on Feb. 14, 2006.

*Date of full bloom.*—Mar. 1, 2006.

*Duration of bloom.*—One to two weeks, dependent on ambient temperature.

*Number per cluster.*—1 to 3 with single flowers most common.

FRUIT

Maturity when described: Firm eating ripe, Jul. 10, 2006.

Date of first picking: Jul. 1, 2006.

Date of last picking: Jul. 13, 2006.

Size: Uniform, large.

*Average diameter axially.*—3" [76 mm.].

*Average diameter across suture plane.*—3½" [89 mm.].

*Average diameter across cheek plane.*—3 9/16" [91 mm.].

*Typical weight.*—9.9 ounces [281 grams].

Form: Slightly asymmetrical, globose to somewhat oblate.

*Longitudinal section form.*—Elliptical to oblate.

*Axial view.*—Round.

Suture: A sharp groove in the stem cavity, a distinct line in a shallow trough along the side, a sharp groove toward the apex extending just beyond the pistil point.

Ventral surface: Rounded, slight bulging along one side, lightly lipped toward the apex.

Lips: Fairly equal toward the apex.

Cavity: Flaring, elongated in the suture plane, suture showing on both sides, Very yellow [82. v.Y] stem markings typical.

*Depth.*—⅜" [9.5 mm.].

*Breadth.*—1⅛" [28.6 mm.].

Base: Truncate.

Apex: Rounded and slightly truncate.

Pistil point: Apical, negligible in length, usually depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Moderate.
*Tendency to crack.*—None observed.
*Color.*—Dark red [16. d.R] over a Moderate reddish orange [37. m.rO] background.
*Down.*—Moderate, short, does not role up when rubbed.
Flesh:
*Color.*—Brilliant yellow [83. brill.Y] with Very red [11. v.R] streaking.
*Surface of pit cavity.*—Moderate pink [5. m.Pk] fibers.
*Amygdalin.*—Moderate.
*Juice.*—Moderate, rich.
*Texture.*—Firm, melting.
*Fibers.*—Abundant, fine.
*Ripens.*—Slightly earlier toward the apex.
*Flavor.*—Mildly acidic and sweet, typically 13 brix, traditional peach taste.
*Aroma.*—Moderate.
*Eating quality.*—Very good.

STONE

Type: Freestone.
Form: Oval.
Hilum: Narrow.
Base: Obtuse, somewhat oblique.
Apex: Obtuse, with an average angle of 110 degrees.
Tips: ⅛" [3.2 mm.] in length with an average tip angle of 75 degrees.
Sides: Slightly unequal.
Surface: Regularly furrowed toward the apex, pitted from the base to slightly beyond the center.
Ridges: Rounded.
External color: Deep yellowish brown [75. deep y.Br].
Pit wall color when cracked: Light yellowish brown [76. l.yBr].
Cavity surface color: Strong yellowish brown [74. s.yBr.].
Average pit wall thickness: ¼" [6.4 mm.].
Average width: 1⅛" [27.0 mm.].
Average length: 1⅜" [34.9 mm.].
Average breadth: ¾" [19.1 mm.].
Tendency to split: None observed.
Kernel:
*Form.*—Oval.
*Skin color.*—Brilliant yellow [83. brill.Y] when first removed.
*Pellicle color.*—Grayish yellow [90. gy.Y].
*Vein color.*—Light olive brown [94. l.OlBr].
*Taste.*—Bitter.
*Viable.*—Yes.
*Average width.*—½" [12.7 mm.].
*Average length.*—13/16" [20.6 mm.].
*Amygdalin.*—Moderate.

Use

Market: Processing, fresh market, and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to its selected seed parent, 'Diamond Princess' (U.S. Plant Pat. No. 7,066) peach, by producing peaches that are nearly globose in shape, freestone in type, yellow in flesh color, acidic and sweet in flavor, and mostly red in skin color, but is distinguished therefrom by requiring much less chilling hours and by producing fruit that is larger in size and that matures about ten days earlier.

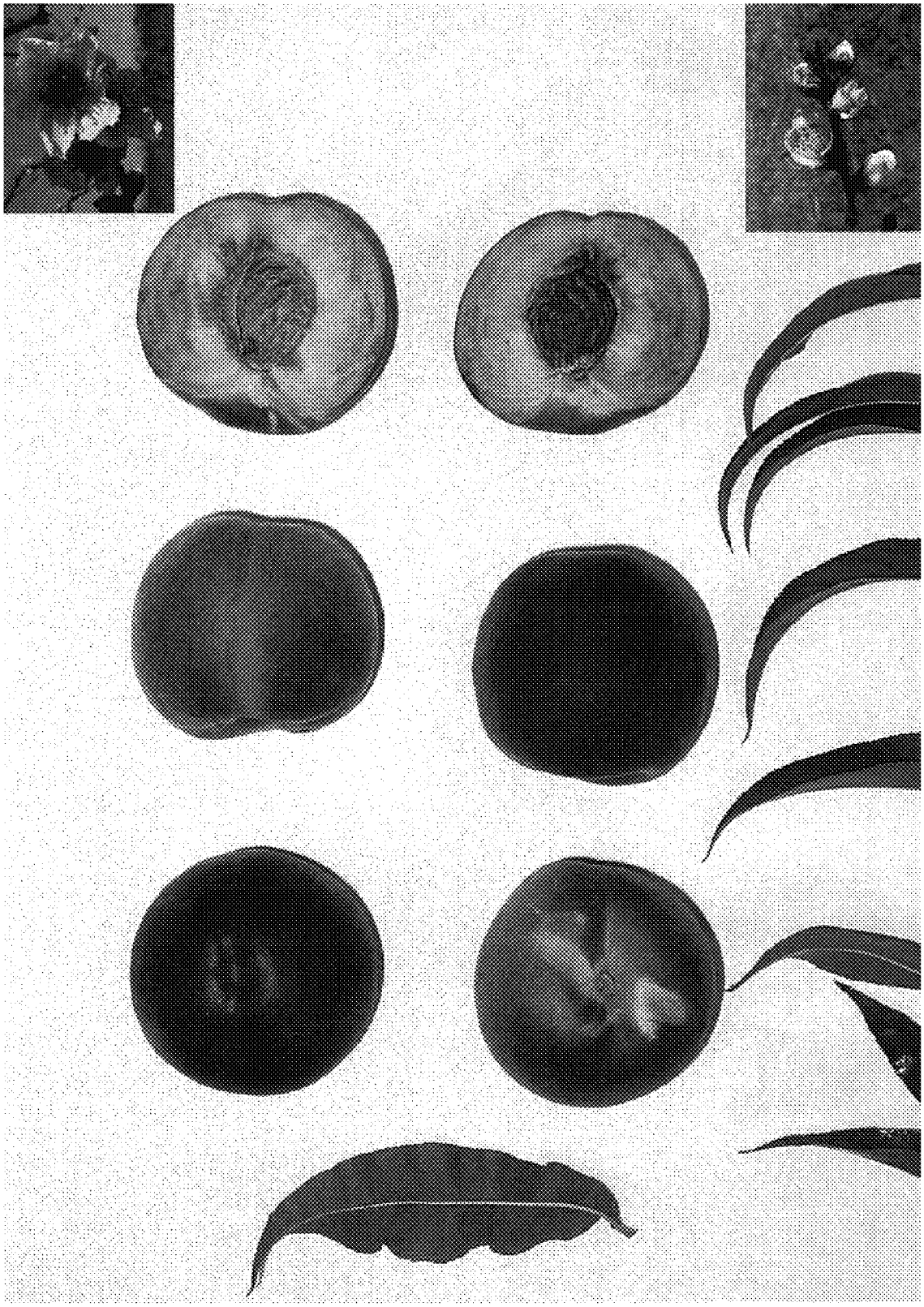

* * * * *